[54] VACCINE FOR THE PREVENTION OF VESICULAR STOMATITIS VIRUS INFECTION

[75] Inventors: Gary P. Wiesehahn; Richard E. Giles, both of Alameda; David R. Stevens, Fremont, all of Calif.

[73] Assignee: Advanced Genetics Research Institute, Oakland, Calif.

[21] Appl. No.: 592,661

[22] Filed: Mar. 23, 1984

[51] Int. Cl.$^4$ ............................................. H61K 39/12
[52] U.S. Cl. ........................................ 424/89; 424/90
[58] Field of Search ............................. 424/89, 88, 90

[56] References Cited

U.S. PATENT DOCUMENTS

| | | | |
|---|---|---|---|
| 3,075,883 | 1/1963 | Scherr et al. | 424/88 |
| 3,083,142 | 3/1963 | Howell et al. | 424/88 |
| 3,149,036 | 9/1964 | Woodhour et al. | 424/88 |
| 3,492,399 | 1/1970 | Prigal | 424/88 |
| 3,594,471 | 7/1971 | Hertzberger et al. | 424/88 |
| 3,629,413 | 12/1971 | Shechmeister et al. | 424/88 |
| 3,790,665 | 2/1974 | Glass et al. | 424/88 |
| 3,869,546 | 3/1975 | Lund | 424/88 |
| 4,069,313 | 1/1978 | Woodhour et al. | 424/88 |
| 4,124,598 | 11/1978 | Hearst et al. | 424/180 |
| 4,196,281 | 4/1980 | Hearst et al. | 424/180 |

OTHER PUBLICATIONS

Hearst et al, C.A. 87: 78962f, (1977) of Nucleic Acids Res. 1977, 4(5): 1339–47.
Nakashima et al, C.A. 92: 72580m, (1980) of J. Virol. 1979, 32(3): 838–844.
Nilsen et al, C.A. 94: 80046y, (1981) of Virology 1981, 109(1): 82–93.
Talib et al, C.A. 96: 211826u, (1982) of Virology 1982, 118(2): 430–8.
Kronenberg, C.A. 98: 105632j, (1983) of EPO 66886, Dec. 15, 1982.
Hanson, C.A. 100: 20043c, (1984) of Med. Virol. 2 Proc. Int. Sympos. (1982), pub. 1983: 45–79.
Holbrook et al, V.B. 28, #3941, (1958) of Proc. 61st Ann. Mtg. U.S. Lvstk. San. Ass. 1957: 308–315.
Correa, V.B. 35, #165, (1965) of Am. J. Vet. Res. 25: 1300–1302, (1964).
Brown et al, V.B. 36, #3495, (1966) of J. Immunol. 96, 537–545, (1966).
Castaneda et al., (1977), Develop. Biol. Standards, 35: 429–436.
Lauerman et al., (1962), Proc. US Livestock San. Assoc., 66: 365–369.
Lauerman and Hanson, (1963), Proc. US Livestock San. Assoc., 67: 483–490.
Isaacs et al., (1977), Biochemistry 16: 1058–1064.
Hanson et al., (1978), J. Gen. Virol. 40: 345–358.
Hanson, in Medical Virology II, Proceedings of the 1982 Intn'l. Symposium . . . de la Maza and Petersons eds. NY, 1983, pp. 45–75.
Hearst and Thiry, (1977), Nuc. Acids. Res., 4: 1339–1347.
Talib and Banerjee, (1982), Virology, 118: 430–438.

*Primary Examiner*—Shep K. Rose
*Attorney, Agent, or Firm*—Townsend and Townsend

[57] ABSTRACT

Novel vaccines for vesicular stomatitis virus are prepared by psoralen inactivation of the live virus under mild conditions in an inert atmosphere. The resulting inactivated virus can be used as a vaccine for inoculation of susceptible hosts to inhibit VSV infection.

13 Claims, No Drawings

VACCINE FOR THE PREVENTION OF VESICULAR STOMATITIS VIRUS INFECTION

BACKGROUND OF THE INVENTION

1. Field of the Invention

Vaccination against both bacterial and viral diseases has been one of the major accomplishments of medicine over the past century. While effective vaccines have been developed for a large number of diseases, development of safe and effective vaccines for a number of other diseases remains problematic. The use of killed microbial agents as a vaccine, although generally safe, will not always be effective if the immunogenic characteristics of the agent are altered. In contrast, the preparation of live, attenuated microbial agents as a vaccine will often provide improved immunologic reactivity, but increases the risk that the vaccine itself will be infectious, e.g., as a result of reversion, and that the organism will be able to propagate and provide a reservoir for future infection. Thus, although much experience has been gained over the years relating to the preparation of bacterial and viral vaccines, the successful preparation of an effective vaccine against a particular infectious agent can never be assured, even when employing techniques which have been successful for other infectious microorganisms.

Vesicular stomatitis is an acute viral disease which is most prevalent in cattle, but which also affects horses, swine and even human beings. Although not generally fatal, the disease can cause substantial economic loss in cattle as a result of diminished milk production in dairy cattle, weight loss in beef cattle, and the like. For that reason, it would be desirable to provide a safe and effective vaccine against vesicular stomatitis for cattle and other susceptible mammalian hosts.

2. Description of the Prior Art

Modified live vesicular stomatitis virus (VSV) vaccines have been developed. See, e.g., Castaneda et al. (1977) Develop. Biol. Standards 35:429-436; Lauerman et al. (1962) Proc. U.S. Livestock San. Assoc. 66:365-369; and Lauerman and Hanson (1963) Proc. U.S. Livestock San. Assoc. 67:483-490. Inactivated VSV vaccines have been developed. See, e.g., Correa (1964) Am. J. Vet. Res. 25:1300-1302; Holbrook and Geleta (1957) Proc. U.S. Livestock San. Assoc. 61:308-815; and Brown et al. (1966) J. Immunol. 96:537-545. None of these modified live or inactivated viral vaccines have been entirely satisfactory.

Isaacs et al. (1977) Biochemistry 16:1058-1064, describe the synthesis of several psoralen derivatives and their photoreactivity with double-standard RNA. Hanson et al. (1978) J. Gen. Virol. 40:345-358 describe the photoreactivity of various psoralen derivatives with animal viruses. Hanson, in *Medical Virology II, Proceedings of the 1982 International Symposium on Medical Virology*, de la Maza and Peterson, ed., New York, Elsevier Biomedical, 1983, pp. 45-75, has cited unpublished data on the inactivation of Bluetongue virus utilizing psoralen photochemistry.

The reactivity of psoralen derivatives with VSV was studied by Hearst and Thiry (1977) Nuc. Acids Res. 4:1339-1347 and Talib and Banerjee (1982) Virology 118:430-438, although neither reference disclosed the preparation or use of psoralen-inactivated VSV vaccines. The preparation and use of other psoralen inactivated viral vaccines are described in copending application Ser. No. 563,939, filed on Dec. 20, 1983.

SUMMARY OF THE INVENTION

Vaccines for inoculation against vesicular stomatitis virus are prepared by irradiating the live virus with light in the presence of an inactivating furocoumarin compound for a time sufficient to render the virus non-infectious. The inactivated virus retains immunogenicity and may be combined with a physiologically acceptable carrier or adjuvant to form the vaccine.

DESCRIPTION OF THE SPECIFIC EMBODIMENTS

Vaccines useful for the inoculation of mammalian hosts, particularly ruminants such as cattle, against vesicular stomatitis virus (VSV) are provided. The vaccines are prepared by inactivation of one or more serotypes of live VSV in an appropriate medium with a sufficient amount of an inactivating furocoumarin to provide for inactivation of the VSV upon subsequent irradiation with long wavelength ultraviolet (UV) radiation. Prior to administration, the vaccines will usually be combined with a physiologically acceptable carrier or adjuvant, and dosages will be in the range from about $10^6$ to $10^9$ pfu/dose. The response to vaccination includes the production of neutralizing antibodies.

Two primary serotypes of VSV are known, but a number of subtypes have also been identified. See, Federer et al. (1967) Res. Vet. Sci. 8:103-117. The primary serotypes are designated New Jersey (VSV-NJ) and Indiana (VSV-I), and three subtypes of VSV-I are designated CoCal, Brazil, and Argentina. The VSV genome codes for five polypeptides designated G, M, N, NS, and L. The G protein is the surface glycoprotein that defines the serologic type. Although there appear to be certain common epitopic sites on the G protein from various serologic types, antibodies produced in response to immunization with one serologic type of virus will generally not neutralize other types of the VSV virus.

Any of the serotypes of VSV may be inactivated and utilized to prepare a vaccine according to the present invention. Serotypes of particular interest will be those prevalent in the geographic area where the vaccine is to be utilized. In the United States, the serotypes of particular interest are VSV-NJ and VSV-I.

In preparing the subject vaccines, sufficient amounts of the desired serotype of virus may be obtained by growing the desired virus in mammalian cell culture. Seed virus may be obtained by isolation from an infected host and used to infect a suitable mammalian cell line. Illustrative cell lines include Vero cells, monkey kidney cells, CCL 10 hamster cells, LMTK⁻ cells, or other cells permissive for VSV and which can be grown in vitro as monolayer cultures or as suspension cultures. The cell cultures are grown to approximately 80% saturation density, and infected with the VSV at a low multiplicity of infection (MOI), usually between about 0.001 and about 0.05, preferably about 0.01. After adsorbing the viral inoculum to the cells by incubation for a limited period of time at a temperature in the range from about 35° to 40° C., an appropriate growth or maintenance medium is added. The cells are incubated at a temperature in the range from about 35° to 40° C., in the presence of about 5% carbon dioxide in air until at least about 50% of the cell culture exhibits cytopathic effect (CPE). CPE is characterized by cell rounding (in monolayers), cell detachment (from monolayers), and cell degeneration. The cultures are gently shaken or swirled to detach cellular mateirial from the culture vessel walls. The harvest material is decanted into centrifuge bottles and clarified by centrifugation at 500 to 1000×g for 20 minutes at 4° C. The clarified virus preparation may be concentrated using conventional ultrafiltration technology (e.g., Millipore Pellicon system XX42ASY60 with a cassette having a nominal exclusion limit of $10^5$ daltons such as Millipore PTHK 000C5).

The particular growth and maintenance medium will be a conventional mammalian cell culture medium, such as Eagle's Minimum Essential Medium or Medium 199, usually supplemented with additives such as broth prepared from dehydrated standard microbial culture media, fetal bovine serum, calf serum, or the like.

The furodoumarins useful for inactivation are primarily illustrated by the class of compounds referred to as psoralens, which includes psoralens and substituted psoralens where the substituents will be: alkyl, particularly having from 1 to 3 carbon atoms, e.g., methyl; alkoxy, particularly having from 1 to 3 carbon atoms, e.g., methoxy; and substituted alkyl having from 1 to 6, more usually from 1 to 3, carbon atoms and from 1 to 2 heteroatoms, which will be oxy, particularly hydroxy or alkoxy having from 1 to 3 carbon atoms, e.g., hydroxy methyl and methoxy methyl, or amino, including mono- and dialkyl amino or aminoalkyl, having a total of from 0 to 6 carbon atoms, e.g., aminomethyl. There will be from 1 to 5, usually from 2 to 4 substituents, which will normally be at the 4, 5, 8, 4' and 5' positions, particularly at the 4' position. Illustrative compounds include 5-methoxypsoralen; 8-methoxypsoralen (8-MOP); 4,5',8-trimethylpsoralen (TMP); 4'-hydroxymethyl-4,5',8-trimethylpsoralen (HMT); 4'-aminomethyl-4,5',8-trimethylpsoralen (AMT); 4-methylpsoralen; 4,4'-dimethylpsoralen; 4,5'-dimethylpsoralen; 4',8-dimethylpsoralen; and 4'-methyloxymethyl-4,5',8-trimethylprosalen. Of particularly interest is AMT.

The furocoumarins may be used individually or in combination. Each of the furocoumarins may be present in amounts ranging from about 0.1 µg/ml to 1 mg/ml, preferably from about 0.5 µg/ml to 100 µg/ml, there not being less than about 1 µg/ml nor more than about 1 mg/ml of furocoumarins.

In carrying out the invention the furocoumarin(s), in an appropriate solvent which is substantially inert and sufficiently polar to allow for dissolution of the furocoumarin(s), are combined with the viral suspension, conveniently a viral suspension in an aqueous buffered medium, such as used for storage. The amount of virus will generally be about $1 \times 10^6$ to $10^{11}$, more usually about $1 \times 10^7$ to $10^9$ and preferably about $1 \times 10^8$ to $5 \times 10^8$ pfu/ml. The furocoumarin will be at a concentration of about 0.001 mg/ml to 0.5 mg/ml, more usually about 0.02 mg/ml to 0.2 mg/ml. The amount of solvent which is used to dissolve the furocoumarin will be sufficiently small so as to readily dissolve in the aqueous viral suspension and have little, if any, effect on the results.

The furocoumarin may be added to the viral suspension is a single addition or in multiple additions, where the virus is irradiated between additions. Usually, the number of additions will be from about 1 to 50, more usually from about 10 to 40, and preferably from about 20 to 40. The total amount of furocoumarin which will be added will be sufficient to provide a concentration of at least about 0.01 mg/ml to about 1 mg/ml, usually not more than about 0.75 mg/ml and preferably not more than about 0.5 mg/ml. Since a substantial proportion of the furocoumarin will have reacted with the RNA between additions, the total concentration of furocoumarin in solution will generally not exceed about 0.2 mg/ml.

The total time for the irradiation will vary depending upon the light intensity, the concentration of the furocoumarin, the concentration of the virus, and the manner of irradiation of the virus, where the intensity of the irradiation may vary in the medium. The total time will usually be at least about 2 hrs. and not more than about 80 hrs., generally ranging from about 10 hrs. to 50 hrs. The times between additions of furocoumarin, where the furocoumarin is added incrementally, will generally vary from about 30 min. to 24 hrs., more usually from about 1 hr. to 3 hrs.

The temperature for the irradiation is preferably under 25° C. more preferably under 20° C. and will generally range from about −10° C. to 15° C., more usually from about 0° to 10° C.

The irradiation is normally carried out in an inert atmosphere, where all or substantially all of the air has been removed. Inert atmospheres include nitrogen, helium, argon, etc.

The light which is employed will generally have a wavelength in the range from about 300 nm to 400 nm. The intensity will generally range from about 0.1 mW/cm$^2$ to about 5 W/cm$^2$.

Optionally, a small amount of a singlet oxygen scavenger may be included during the virus inactivation. Singlet oxygen scavengers include ascorbic acid, dithioerythritol, sodium thionite, glutathione, etc. The amount of scavenger will generally be at a concentration of about 0.001M to 0.5M, more usually at about 0.01M to 0.1M, where the addition may be made in a single or multiple additions.

During irradiation, the medium may be maintained still, stirred or circulated and may be either continuously irradiated or be subject to alternating periods of irradiation and non-irradiation. The circulation may be in a closed loop system or in a single pass system ensuring that all of the sample has been exposed to irradiation.

It may be desirable to remove the unexpended furocoumarin and/or its photobreakdown products from the irradiation mixture. This can be readily accomplished by one of several standard laboratory procedures such as dialysis across an appropriately sized membrane or through an appropriately sized hollow fiber system after completion of the irradiation. Alternatively, one could use affinity columns for one or more of the low molecular weight materials to be removed.

The inactivated vaccine may then be formulated in a variety of ways for use for inoculation. The concentration of the virus will generally be from about $10^6$ to $10^9$ pfu/ml, as determined prior to inactivation, with a total dosage of at least $10^5$ pfu/dose, usually at least $10^6$ pfu/dose, preferably at least $10^7$ pfu/dose. The total dosage will usually be at or near about $10^9$ pfu/dose, more usually being about $10^8$ pfu/dose. The vaccine may include cells or may be cell-free. It may be an inert physiologically acceptable medium, such as ionized water, phosphate-buffered saline, saline, or the like, or may be administered in combination with a physiologically acceptable immunologic adjuvant, including but not limited to mineral oils, vegetable oils, mineral salts and immunopotentiators, such as muramyl dipeptide. The vaccine may be administered subcutaneously, intramuscularly, or intraperitoneally. Usually, a specific dosage at a specific site will range from about 0.1 ml to 4 ml, where the total dosage will range from about 0.5 ml to 8 ml. The number of injections and their temporal spacing may be highly variable, but usually 1 to 3 injections at 1, 2 or 3 week intervals are effective.

The following examples are offered by way of illustration, not by way of limitation.

EXPERIMENTAL

Materials and Methods

A. Virus Growth and Tissue Culture

Hamster cells [BHK-21(C-13), Americal Type Culture Collection (ATCC), CCL 10] or Vero monkey cells (ATCC No. CCL81) are grown as monolayers in plastic cell culture vessels in Eagle's Minimum Essential Medium with Earle's salts and non-essential amino acids (MEN) supplemented with 10% heat inactivated calf serum ($C^i$) and 10% tryptose phosphate broth (Tp, e.g., Difco 0060) or 5% heat inactivated fetal bovine serum ($F^i$). Cell cultures are used to produce live VSV-NJ from master seed virus obtained from the ATCC (VR-159). Cells are grown in culture vessels to 80% to 100% confluency (approximately $2\times10^5$ cells per $cm^2$ of growth surface area) using standard mammalian cell culture techniques. Generally plastic roller bottles (e.g., Corning No. 25140-850) with a growth surface area of 850 $cm^2$ containing 100 ml of MEN supplemented with 10% $C^i$ and 10% Tp and $1\times10^8$ to $2\times10^8$ CCL 10 cells/bottle are used for virus production although other permissive cells, other cell culture vessels, other cell culture media or other supplements may be used. The cell cultures are initiated by seeding approximately $1\times10^7$ cells into 100 mls of growth medium in a roller bottle on a roller bottle rotator at 0.25 to 2 rpm at 35° C. The cultures are grown to 80% to 100% confluency over a six to ten day period with a medium change every two to four days.

When the monolayers are 80% to 100% confluent the culture medium is removed and the monolayer is infected with approximately $1\times10^6$ to $2\times10^6$ plaque forming units (pfu) of VSV in 20 mls of MEN. The multiplicity of infection (MOI) is approximately 0.01. The MOI may range from 0.001 pfu/cell to 0.05 pfu/cell. The virus inoculum is adsorbed to the cells by incubation at 35° C. to 38° C. for one hour at 1 to 5 rpm. One hundred mls of MEN containing 10% YELP supplement (v/v) is added per roller bottle. YELP supplement contains: yeast extract (e.g., BBL 11929), 5 g/liter; lactalbumin hydrolysate (e.g., GIBCO 670–1800), 25 g/liter; and Bacto-Peptone (e.g., Difco 0118), 50 g/liter. The post-infection incubation is at 35° C. to 38° C. in 5% $CO_2$/95% air with rotation. Sixteen to forty-eight hours post-infection, VSV cytopathic effect (CPE) is evident. The CPE is characterized by cell rounding, cell detachment, and cell degeneration. When visual or microscopic examination indicates that at least 50% of the cell monolayer exhibits CPE, the contents of the roller bottle are swirled to remove loosely attached materials from the roller bottle walls. The harvest material is decanted from the roller bottles into centrifuge bottles. The crude virus harvest is clarified by centrifugation at 500 to 100×g for 20 minutes, at 4° C.

The clarified virus preparation may be concentrated by ultrafiltration using a Pellicon cassette system (Millipore XX42ASY60) with a cassette having a nominal exclusion limit of $10^5$ daltons (Millipore PTHK 000C5). The Pellicon cassette system is sterilized by filling the assembled unit with 1N NaOH and incubating the unit 12 to 24 hours at room temperature. The NaOH solution is pumped out of the cassette system and the system is flushed with two to four liters of sterile $H_2O$. The assembly and operation of the Pellicon system are in accordance with the instructions furnished by the manufacturer. All steps in the concentration are performed aseptically. The clarified virus is concentrated 15 to 40 fold, dimethylsulfoxide (e.g., Sigma D-5879) is added to a final concentration of 7.5% v/v and suitable aliquots of the virus stored frozen at −80° C. to −100° C.

B. Virus Assay

Confluent monolayers of LMTK− or Vero (ATCC CCL 81) cells are prepared in 6 cm diameter mammalian cell culture plastic petri dishes (e.g., Corning #25010) or other convenient cell culture vessels. The growth medium used for LMTK− cells is alpha ME (alpha modified Eagles Minimum Essential Medium, Earle's Salts )+10% $F^i$, and the growth medium used for Vero cells is MEN+5% $F^i$. Ten fold serial dilutions of virus samples are made by adding 0.5 ml of the virus sample to 4.5 mls of phosphate buffered saline (pH 7.2 to 7.4) containing 2% $F^i$ in a screw cap tube. The growth medium is removed from a 6 cm culture dish cell monolayer, 0.1 ml of virus sample (undiluted or diluted) is added, and the virus is adsorbed to the monolayer for 1 to 2 hours at 35° C. to 38° C. Two or more monolayers are used for each sample. Five ml of overlay medium is added per 6 cm culture dish. The overlay medium is prepared by mixing equal parts of solution A [100 ml 2X MEM with L-glutamine, (e.g., GIBCO #320–1935), +10 ml $F^i$] and 1.8% Noble Agar (e.g., Difco 0142) in deionized $H_2O$ at 44° C. to 45° C. The cultures are incubated at 35° C. to 38° C. in 5% $CO_2$ in air for 24 hours, and then a second overlay containing Neutral Red at a final concentration of 0.005% is added. Plaques are counted on day 2 and day 3 post-infection. The virus titer in pfu/ml is calculated by multiplying the average number of plaques per dish by the reciprocal of the dilution. The pfu/ml is the value used to determine the amount of virus needed to infect cells at a MOI of approximately 0.01. The pfu/ml in a virus preparation prior to inactivation is used to determine the immunizing dose.

C. VSV Inactivation

The thawed stock of VSV is pipetted into sterile T-150 tissue culture flasks (e.g., Corning 25120; nominally 25 ml into each of four flasks). To each flask is added 0.25 ml of 4'-aminomethyl-4,5',8-trimethylpsoralen (AMT) stock solution (stock solution is 1 mg/ml AMT dissolved in sterile, deionized water). Each flask is allowed to equilibrate in an argon atmosphere for at least 10 minutes. After equilibrium, a stream of argon gas is directed into each flask for at least two minutes. The flasks are then tightly capped and placed under a long wavelength untraviolet (320 nm to 400 nm) light source (e.g., GE BLB fluorescent bulbs) at a temperature between 0° C. and 20° C. for approximately 11 hours. The incident light intensity is approximately 1 mW/$cm^2$ (measured by an Ultra-Violet Products model J-221 long wavelength UV meter).

After the irradiation is completed, the flasks are removed from the light source and an additional 0.25 ml of AMT stock solution is mixed into each flask. The contents of each flask are pipetted into new, sterile T-150 flasks, and the flasks are again flushed with argon and irradiated for an additional 11 hours. This procedure is repeated three more times until five additions (a total of approx. 50 μg/ml) of AMT have been performed, the virus sample has been irradiated for at least 55 hours, and at least four flask changes have been performed.

After all of the irradiations have been completed, the contents of the flasks are aseptically transferred to a common sterile container and stored at −85° C.

Results

A. Assessment of Inactivation

Suckling mice (0 to 10 days old) are inoculated intracerebrally with 0.02 ml of the psoralen-inactivated VSV-NJ using a tuberculin syringe and a 28 or 30 gauge needle. Each vaccine lot is tested in four to nine suckling mice. The mice are observed daily for a minimum of seven days. Residual low-level live VSV kills suckling mice in two to five days. The sensitivity of this array is approximately 1 to 5 pfu of live VSV per intracerebral dose. Inactivated VSV-NJ vaccine is considered save (inactivated) if all inoculated suckling mice survive the seven day observation period. The VSV-NJ vaccine batches used hereinafter each passed the suckling mouse safety test prior to use.

B. Virus Neutralization in Mice Vaccinated with Psoralen-inactivated VSV-NJ Vaccine Groups of ten adult white mice each were injected using three immunological adjuvants (aluminum hydroxide gel, incomplete Freund's, or oil emulsion) with one of three psoralen-inactivated VSV-NJ vaccine doses ($10^9$, $10^8$, or $10^7$ pfu/dose). The oil emulsion was prepared as described by Stone et al. (1978) Avian Dis. 22:666–674. All mive were injected IP once each, on day 0 and day 21. Serum samples were collected from the orbital sinus on day 20 and on day 33 and pooled serum samples were assessed for serum neutralization (SN) activity by standard procedures. See, Castaneda et al. (1964) Proc. U.S. Livestock San. Assoc. 68:455–468. Serum samples were negative for neutralizing antibodies to VSV-NJ prior to vaccination.

The vaccine with oil emulsion adjuvant induced the highest SN titers after one injection. All three vaccine doses, regardless of adjuvant, induced SN titers of at least 1:2000 after two injections. Serum dilutions were tested for SN activity only to 1:2560. The results are set forth in Table I.

TABLE I

Virus Neutralization Indices* of Mouse Sera After One and Two Injections of Psoralen-Inactivated VSV-NJ Vaccine

| Adjuvant | No. of Injections | $Log_{10}$ of Vaccine Concentration (pfu/dose) | | |
|---|---|---|---|---|
| | | 7 | 8 | 9 |
| Aluminum hydroxide gel | 1 | 67* | 905 | 905 |
| Aluminum hydroxide gel | 2 | >2560 | 2560 | >2560 |
| Freund's Incomplete | 1 | 226 | 57 | 905 |
| Freund's Incomplete | 2 | 2033 | >2560 | >2560 |
| Oil Emulsion | 1 | >2560 | >2560 | 2357 |
| Oil Emulsion | 2 | >2560 | >2560 | >2560 |

*Virus neutralization index is the reciprocal of the serum dilution that neutralized 32 TCID$_{50}$ of VSV-NJ.

C. Virus Neutralization in Hamsters Vaccinated with Psoralen-inactivated VSV-NJ Vaccine Groups of five MHA hamsters each were injected with either $10^9$, $10^8$, or $10^7$ pfu psoralen-inactivated VSV-NJ per dose, with or without aluminum hydroxide adjuvant (1:1). All hamsters were injected intramuscularly (IM) once each, on day 0 and again on day 21. Pooled serum samples were collected on day 21 and on day 34 for serum neutralization testing by standard procedures. Serum neutralizing antibodies were elicited by all three vaccine doses tested, with or without aluminum hydroxide adjuvant (see Table II).

TABLE II

Virus Neutralization Indices* of Hamster Sera After One and Two Injections of Psoralen-Inactivated VSV-NJ Vaccine

| Adjuvant | No. of Injections | $Log_{10}$ of Vaccine Concentration (pfu/dose) | | |
|---|---|---|---|---|
| | | 7 | 8 | 9 |
| None | 1 | 134* | 134 | 1076 |
| None | 2 | 1280 | 1810 | >2560 |
| Aluminum hydroxide gel | 1 | 538 | 538 | >2560 |
| Aluminum hydroxide gel | 2 | 1810 | 1920 | 2560 |

*Virus neutralization index is the reciprocal of the serum dilution that neutralized 32 TCID$_{50}$ of VSV-NJ.

C. Live VSV-NJ Challenge of Mice Vaccinated with Psoralen-inactivated VSV-NJ Vaccine Three groups of fourteen, sixteen and seventeen adult white mice were each injected with either $10^7$, $10^6$ or $10^5$ pfu psoralen-inactivated VSV-NJ per dose, respectively, using oil emulsion adjuvant with all injections. Each mouse was injected once IP (day 0). Pooled serum samples were collected on day 0 and again on day 21, and these samples were tested for SN antibody titers by standard procedures (see Table III).

TABLE III

Virus Neutralization Indices* of Mouse Sera After One Injection With Psoralen-Inactivated VSV-NJ Vaccine, Using Oil Emulsion Adjuvant

| Day | $Log_{10}$ of Vaccine Concentration (pfu/dose) | | |
|---|---|---|---|
| | 5 | 6 | 7 |
| 0 | —* | — | — |
| 21 | — | — | 40 |

*Virus neutralization index is the reciprocal of the serum dilution that neutralized 56 TCID$_{50}$ of VSV-NJ Each group of mice was subdivided into three groups of about five mice each. Each mouse group was challenged with either 1, 10 or 100 minimum lethal doses (MLD) of live VSV by intracerebral inoculation on day 33.

Two of five mice that were immunized with $10^6$ pfu psoralen-inactivated VSV-NJ survived a one MLD VSV challenge but five of five mice that were immunized with $10^7$ pfu psoralen-inactivated VSV-NJ vaccine survived both a 1 or 10 MLD VSV challenge. One of four mice that were vaccinated at $10^7$ pfu/dose psoralen-inactivated VSV-NJ survived a 100 MLD VSV challenge. The results (no. dead/no. challenged) are set forth in Table IV.

TABLE IV

Live VSV-NJ Challenge of Mice Injected with Psoralen-Inactivated VSV-NJ

| Dose Psoralen-Inactivated VSV-NJ Vaccine | Challenge Dilution | | |
|---|---|---|---|
| | $10^{-5}$ (1 MLD) | $10^{-4}$ (10 MLD) | $10^{-3}$ (100 MLD) |
| $10^7$ pfu | 0/5* | 0/5 | 3/4 |
| $10^6$ pfu | 3/5 | 4/5 | 3/6 |
| $10^5$ pfu | 5/5 | 4/5 | 7/7 |

*Number dead/number challenged

E. Virus Neutralization in Cattle Vaccinated with Psoralen-inactivated VSV-NJ Vaccine Four groups of six mature beef cattle each were injected with either $10^8$ or $10^7$ pfu/dose psoralen-inactivated VSV-NJ vaccine, with or without aluminum hydroxide adjuvant (1:1). Each cow was vaccinated subcutaneously (SQ) on day 0 and again on day 21. A control group consisted of an additional six cattle that were inoculated only with adjuvant on day 0 and again on day 21. All cattle were bled on days 0, 14, 21, and 35. Serum from each animal was tested for SN antibodies to VSV-NJ by standard procedures.

The aluminum hydroxide adjuvant was required to elicit significant SN titers in cattle, and $10^8$ pfu/dose induced the highest responses. The results are set forth in Table V. A VSV-NJ virus neutralization index greater than 1000 has been reported to represent protection against $10^6$ ID$_{50}$ of live VSV by intralingual challange in cattle. See, Castaneda et al. (1964) Proc. U.S. Livestock San. Assoc. 68:455–468.

TABLE V

Virus Neutralization Indices* From Cattle Injected With Psoralen-Inactivated VSV-NJ Vaccine

| Group | Treatment | Animal | 0** | 14 | 21** | 35 |
|---|---|---|---|---|---|---|
| A | $10^8$ pfu/dose + Al(OH)$_3$ | 310 | — | 16 | 16 | 256 |
| | | 731 | — | — | — | >16 |
| | | 911 | — | 128 | 64 | 2048 |
| | | 921 | — | 8 | 8 | 1024 |
| | | 943 | — | 16 | 32 | 1024 |
| | | 944 | — | 32 | 32 | 512 |
| B | $10^7$ pfu/dose + Al(OH)$_3$ | 303 | — | — | — | 256 |
| | | 304 | — | — | — | 64 |
| | | 308 | 4 | 4 | 8 | 512 |
| | | 542 | — | — | — | 8 |
| | | 914 | — | 16 | 4 | 512 |
| | | 1670 | — | — | — | >128 |
| C | Controls | 305 | — | — | — | — |
| | | 309 | — | — | — | — |
| | | 314 | — | — | — | — |
| | | 315 | — | — | — | — |
| | | 316 | — | — | — | — |
| | | 318 | — | — | — | — |
| D | $10^8$ pfu/dose without adjuvant | 302 | — | — | — | 4 |
| | | 611 | — | — | — | 4 |
| | | 714 | — | — | — | 8 |
| | | 732 | — | — | — | 4 |
| | | 747 | — | — | — | — |
| | | 996 | — | — | — | 32 |
| E | $10^7$ pfu/dose without adjuvant | 101 | — | — | — | — |
| | | 312 | — | — | — | 4 |
| | | 616 | — | — | — | — |
| | | 721 | — | — | — | — |
| | | 722 | — | — | — | — |
| | | 1944 | — | — | — | — |

*Virus neutralization index is the reciprocal of the serum dilution that neutralized 32 TCID$_{50}$ of VSV-NJ.
**Immunization days.

According to the present invention, furocoumarin-inactivated VSV retains its immunogenicity, particularly as to those sites which elicit an immune response to the live virus, and may be effectively utilized for inoculating a host against subsequent VSV infection. The inactivated viruses of the present invention are completely non-infectious and may be administered safely to a host for vaccination.

Although the foregoing invention has been described in some detail by way of illustration and example, for purposes of clarity of understanding, it will be obvious that certain changes and modifications may be practiced within the scope of the appended claims.

What is claimed is:

1. A vaccine useful for inoculation of a mammalian host susceptible to infection by vesicular stomatitis virus (VSV), which vaccine comprises an immunologic adjuvant and about a $10^6$ to $10^9$ pfu/dose effective dosage amount of at least one inactivated VSV serotype, wherein the VSV has been inactivated by exposure to long wavelength ultraviolet light at a temperature below about 40° C. under conditions excluding free oxygen and in an inert atmosphere in the presence of an inactivating furocoumarin for a time sufficient to render said VSV non-infectious, whereby the immunogenicity is substantially retained.

2. A vaccine according to claim 1, wherein said furocoumarin is 4'-aminomethyl-4,5',8-trimethylpsoralen.

3. A vaccine according to claim 2, wherein said VSV is of the New Jersey serotype.

4. A vaccine according to claim 1, wherein said vaccine includes aluminum hydroxide as an adjuvant.

5. A vaccine according to claim 1, wherein said vaccine includes oil emulsion adjuvant.

6. A vaccine according to claim 1, wherein said VSV is inactivated in the presence of a singlet oxygen scavenger.

7. A vaccine according to claim 1, wherein said VSV is grown in substantially confluent monolayers of host cells immediately prior to inactivation.

8. A vaccine useful for inoculation of a mammalian host susceptible to infection by vesicular stomatitis (VSV), which comprises VSV New Jersey serotype inactivated by irradiation with long wavelength ultraviolet light in the presence of 4'-amino-methyl-4,5'-8-trimethylpsorlen at a temperature in the range of about −10° to 15° C. for a time sufficient to render said VSV non-infectious under conditions substantially excluding free oxygen and in an inert atmosphere in which the VSV substantially retains its immunogenicity, said VSV being present at about $10^6$ to $10^8$ pfu/dose in a physiologically acceptable immunologic adjuvant carrier.

9. A vaccine according to claim 8, wherein said vaccine includes aluminum hydroxide as an adjuvant.

10. A vaccine according to claim 8, wherein said vaccine includes oil emulsion adjuvant.

11. A vaccine according to claim 8, wherein said VSV is inactivated in the presence of a singlet oxygen scavenger.

12. A vaccine useful for inoculation of a mammalian host susceptible to infection by vesicular stomatitis virus (VSV), which vaccine comprises an immunologic adjuvant and about a $10^6$ to $10^9$ pfu/dose effective dosage amount of at least one inactivated VSV serotype, wherein the VSV has been inactivated by exposure to long wavelength ultraviolet light in the substantial absence of oxygen at a temperature below about 40° C. in the presence of an inactivating furocoumarin for a time sufficient to render said VSV non-infectious.

13. A vaccine useful for inoculation of a mammalian host susceptible to infection by vesicular stomatitis (VSV), which comprises VSV New Jersey serotype inactivated by irradiation in the substantial absence of oxygen with low wavelength ultraviolet light in the presence of 4'-aminomethyl-4,5',8-trimethylpsoralen at a temperature in the range of about $-10°$ C. to $15°$ C. for a time sufficient to render said VSV non-infectious, said VSV being present at about $10^6$ to $10^8$ pfu/dose in a physiologically acceptable immunologic adjuvant carrier.

* * * * *